United States Patent [19]
Christinaki et al.

[11] Patent Number: 5,273,983
[45] Date of Patent: Dec. 28, 1993

[54] CYCLOHEXYLBENZAMIDE DERIVATIVES, THEIR PREPARATIONS AND THEIR USE AS GASTROINTESTINAL STIMULANTS

[75] Inventors: Hélène Christinaki, Meudon-la-Foret; Thierry Bouyssou, Plaisir; Michel Pairet, Elancourt; Alain Renaud, Rueil Malmaison, all of France

[73] Assignee: Laboratories Jacques Logeais, Issy les Moulineaux, France

[21] Appl. No.: 857,395

[22] Filed: Mar. 25, 1992

[30] Foreign Application Priority Data

Apr. 2, 1991 [FR] France ............... 91 03959

[51] Int. Cl.$^5$ ............... A61K 31/445; C07D 405/08; C07D 211/32
[52] U.S. Cl. ............... 514/331; 514/320; 514/327; 546/196; 546/221; 546/234
[58] Field of Search ............... 546/196, 234, 240, 221; 514/320, 327, 331

[56] References Cited

FOREIGN PATENT DOCUMENTS

| | | |
|---|---|---|
| 0076530 | 4/1983 | European Pat. Off. . |
| 0094742 | 11/1983 | European Pat. Off. . |
| 0222533 | 5/1987 | European Pat. Off. . |
| 2264530 | 10/1975 | France . |
| 2370722 | 6/1978 | France . |
| 1015921 | 1/1966 | United Kingdom . |

OTHER PUBLICATIONS

Ellis and Lee "Esters and Amides from Mannich Ketanes" J. Med. Chem. 10 (1) 130–131 (1967).

*Primary Examiner*—C. Warren Ivy
*Assistant Examiner*—Celia Chang
*Attorney, Agent, or Firm*—Young & Thompson

[57] ABSTRACT

Novel N-cyclohexylbenzamide derivatives of formula:

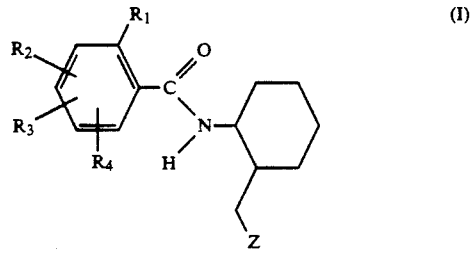

(I)

where $R_1$ represents an alkoxy radical capable of cyclizing with the aromatic ring;

$R_2$, $R_3$ and $R_4$ each independently represent hydrogen, a halogen or an alkoxy, amino, alkylamino or alkyl-carbonylamino group, and Z represents a differently substituted piperidinyl group; and their addition salts with pharmaceutically acceptable acids.

The compounds of formula I are powerful gastrointestinal motility stimulants.

11 Claims, No Drawings

CYCLOHEXYLBENZAMIDE DERIVATIVES, THEIR PREPARATIONS AND THEIR USE AS GASTROINTESTINAL STIMULANTS

Numerous orthopamides are known for various pharmacological properties, such as, for example, the neuroleptic agents derived from Sulpiride (U.S. Pat. No. 3,342,826) or the anti-emetic agents and gastric motility stimulants such as Metoclopramide (BE-A-620,543). The latter product is known to act on the dopaminergic processes of the central nervous system.

More recent compounds of the benzamide family, such as Cisapride (EP-A-076,530) or Renzapride (EP-A-094,742) are known for their activity on the digestive motility in the absence of central antidopaminergic effects.

In addition, compounds corresponding to the general formula

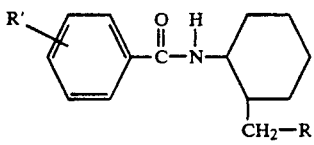

in which R is a tertiary amino group, in particular a piperidino group, and R' is an alkoxy group in the para- or meta-position on the benzamide ring, are known for their anticonvulsant properties (GB-A-1,015,921).

We have now discovered that the compounds which are represented by the general formula (I) defined below and which differ from the above compounds in particular in that they contain a polysubstituted aromatic ring and in particular an alkoxy group in the ortho-position are powerful gastro-intestinal motility stimulants and devoid of central dopaminergic antagonistic activity, while the compounds described which do not have this substitution do not have such an activity. By way of example, a compound A of the type described in GB-A-1,015,921, corresponding to the general formula I but with $R_1=R_3=R_4=H$ and $R_2=4$-pentyloxy do not show any activity on the intestinal motility at the highest dose used to test the compounds according to the invention.

The present invention thus relates to novel benzamides corresponding to the general formula (I)

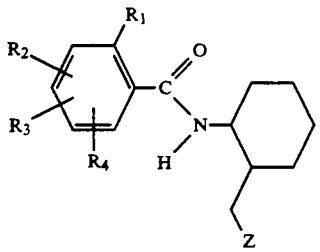

in which:

$R_1$ is selected from $C_1$-$C_4$ alkoxy, methoxy ($C_1$-$C_3$ alkoxy), $C_3$-$C_4$ alkenyloxy and $C_5$-$C_6$ cycloalkoxy groups, or $R_1$ and $R_2$, in the 3-position, together and with the aromatic ring to which they are bonded form a 2,3-dihydrobenzofuran ring, $R_2$, $R_3$ and $R_4$ are selected independently of one another from a hydrogen atom, a halogen atom and hydroxy, $C_1$-$C_3$ alkoxy, amino, ($C_1$-$C_3$ alkyl)amino or di($C_1$-$C_3$alkyl) amino and ($C_1$-$C_3$ alkyl)carbonylamino groups, and Z is selected from piperidinyl groups and piperidinyl groups substituted in the 4-position by a hydroxy, $C_1$-$C_3$ alkoxy, hydroxyethyl, ($C_1$-$C_3$ alkoxy)ethyl and ($C_1$-$C_3$ alkoxy)methyl groups, a $C_1$-$C_4$ alkyl group or two $C_1$-$C_3$ alkyl groups, their N-oxides, in particular those in which the N-oxide is carried by Z, and their addition salts with pharmaceutically acceptable acids.

The present invention encompasses the stereoisomers of cis relative configuration and tran relative configuration formed by the substituents of the cyclohexyl ring, as well as the corresponding enantiomers.

In the present invention, alkyl or alkoxy group denotes either straight-chain or branched groups or groups having a cyclic part.

In the present invention, "pharmaceutically acceptable salts" denotes the addition salts with acids which give the biological properties of the compounds without having an undesirable effect. These salts may be, in particular, those formed with inorganic acids, such as hydrochloric acid, hydrobromic acid, sulphuric acid, nitric acid or phosphoric acid; acid metal salts, such as disodium orthophosphate and monopotassium sulphide, and organic acids, such as formic acid, acetic acid, propionic acid, glycolic acid, oxalic acid, fumaric acid, lactic acid, succinic acid, tartaric acid, malic acid and pamoic acid.

The preferred compounds of formula I are those which have an alkoxy substituent, in particular a methoxy, ethoxy or cyclopropylmethoxy group, in the 2-position, an amino substituent in the 4-position and chloro in the 5-position on the aromatic ring.

Amongst these benzamides, the compounds of formula (I) in which Z is a piperidino group, preferably substituted in 4-position by one or two methyl groups or by a hydroxyl group, are more particularly preferred.

The preferred compounds therefore have the structure (IV) or (V).

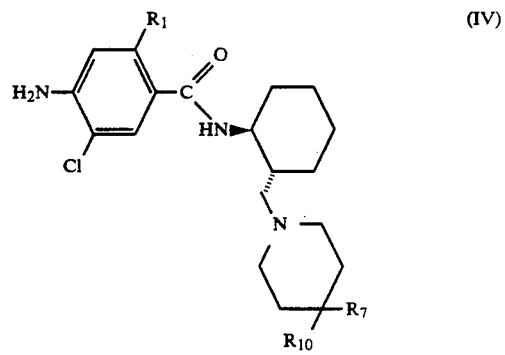

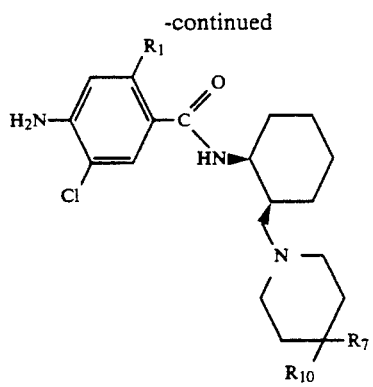

(V)

in which $R_7$=CH$_3$, $R_{10}$=H or $R_7$=CH$_3$=$R_{10}$ or $R_7$=OH, $R_{10}$=H and $R_1$=OCH$_3$, OC$_2$H$_5$ or cyclopropylmethoxy.

The compounds of formula (I) may be obtained by a condensation reaction between a benzoic acid of formula VI, where $R_1$, $R_2$, $R_3$ and $R_4$ have the same definitions as above, and a cyclohexylamine of formula (VII) of cis or trans configuration with Z having the same definitions as in formula (I) in accordance with the equation

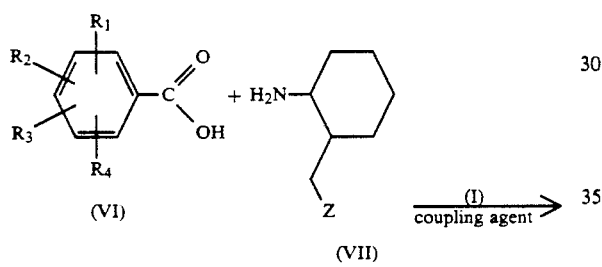

The coupling agent may be carbonyldiimidazole or dicyclohexylcarbodiimide used in solvents such as methylene chloride or tetrahydrofuran or even pyridine.

If the benzoic acid of the formula VI does not carry a basic amino or alkylamino functional group, it may be activated in the form of the acid chloride by the action of thionyl chloride in a solvent such as toluene, before reaction with the amine of formula VII.

The amine of formula VII may be obtained by several different routes leading either to the diastereoisomer of cis configuration of formula VII' or to the diastereoisomer of trans configuration of formula VII''.

Route 1

The compound of formula VII' may be obtained by reaction of the cis-amine of formula VIII' with the aid of a hydride such as lithium aluminium hydride in tetrahydrofuran

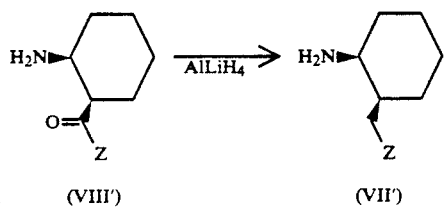

Similarly, the compound of formula VII'' may be obtained by reduction of the amide of formula VIII''

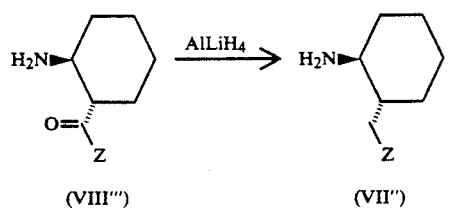

The compounds VIII are obtained in three steps from the corresponding β-amino acids in accordance with the following equation:

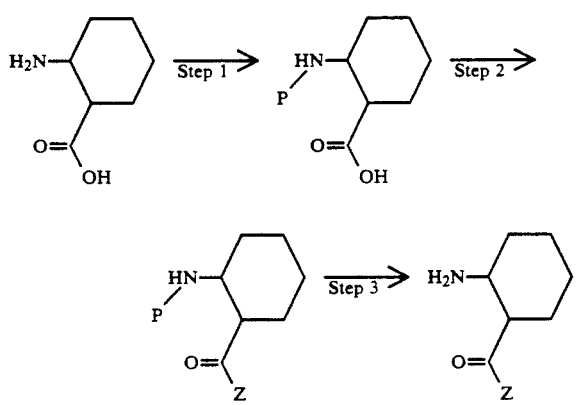

Step 1 consists in protecting the primary amine by an acyl group such as trifluoroacetyl, as already described in the literature (Act. Chim. Acad. Scient. Hung 99 (2), 175–192 (1979)) or urethane group, such as benzyloxycarbonyl or t-butoxycarbonyl, or any other group commonly used in peptide synthesis.

Step 2 comprises a condensation reaction of the group Z, either by one of the methods described for the preparation of (I) or even by the intermediate formation of a mixed anhydride, obtained from chloroformates.

Step 3 consists in removing the protection from the amine functional group, using an alkaline medium in the case of a trifluoroacetyl, a catalytic hydrogenation in the case of a benzyloxycarbonyl group, or trifluoroacetic acid in methylene chloride in the case of a t-butoxycarbonyl group.

The starting β-amino acids of cis or trans relative configuration are obtained by the methods already described in the literature.

The preparation of the optically pure compounds VII may be carried out by stereoselective crystallisation of the N-protected, for example N-benzoylated, β-amino acids, in the form of a salt obtained with the aid of an optically active amine, such as cinchonodine. A resolution of this type is described in J. Chem. Soc. (1970), 1597–1600. The optically pure β-amino acid is then converted to diamine VII by the sequence of following reactions:

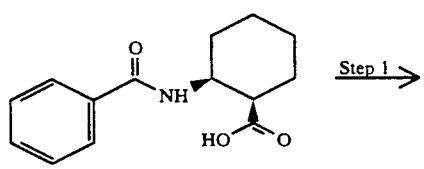

(+) or (−)

Step 1 →

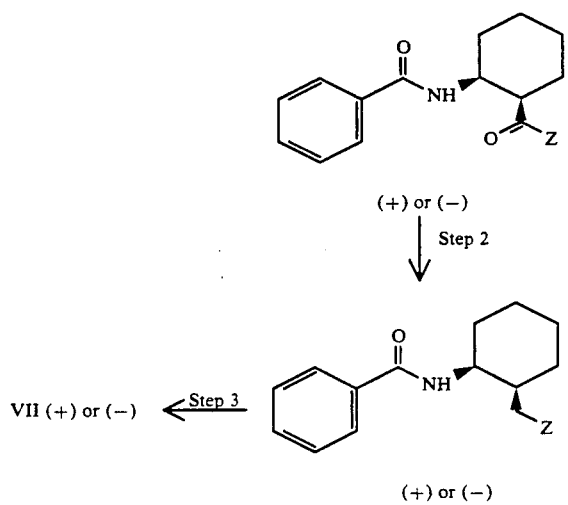

(+) or (−)

↓ Step 2

VII (+) or (−)  ← Step 3

(+) or (−)

Step 1 comprises a condensation reaction of the group Z by the methods already described. Step 2 consists in selective reduction of the tertiary amide functional group by a hydride such as AlLiH Step 3 consists in hydrolysing the benzoyl group in an aqueous acid medium. The sequence of reactions is carried out on one or the other enantiomers.

Another method for obtaining optically pure compounds consists in carrying out a stereoselective hydrolysis of dimethyl 1,2-cyclohex-4-enedicarboxylate with the aid of a lipase such as pig liver lipase. Optically pure β-amino acids are obtained after Curtius arrangement carried out on the acid ester.

A methodology of this type is described in Tetrahedron Letters (1984), 25, 2557-2560. The cyclohexene double bond is reduced by hydrogenation in the presence of a catalyst, such as palladium-on-charcoal. This step may be carried out at any time in the sequence of operations, depending on the protective groups used. These β-amino acids are converted to diamine VII by the methods described above.

Route 2

The compounds of formula VII may also be obtained by a Mannich reaction on cyclohexanone, followed by a reductive amination reaction proceeding either via the oxime or via an imine such as that obtained with benzylamine, in accordance with the equation:

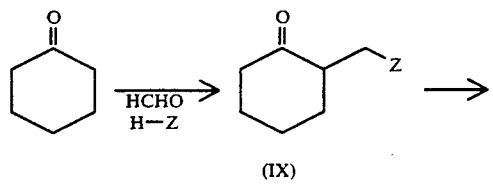

(IX)

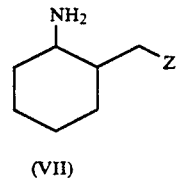

(VII)

In this case a mixture of the cis and trans compounds is obtained, the proportions of which vary with the reducing agent used in the final step. By way of example, the oxime obtained from the ketone of formula (IX) predominantly yields a trans-amine VII" by reduction with the aid of sodium in isoamyl alcohol and predominantly yields a cis-amine VII' following reduction using the hydride AlLiH$_4$.

Route 3

The compounds of general formula VII" may also be obtained from the ketone IX by reduction with the aid, for example, of K selectride (of formula K(s-Bu)-3BH) in tetrahydrofuran.

The cis-alcohol obtained is then activated, for example via a mesylate, and a functional group capable of generating a primary amine, such as an azide or phthalimide group, is then introduced as a substituent. The precursor is then converted to amine by the methods known from the literature. The reaction equation is as follows:

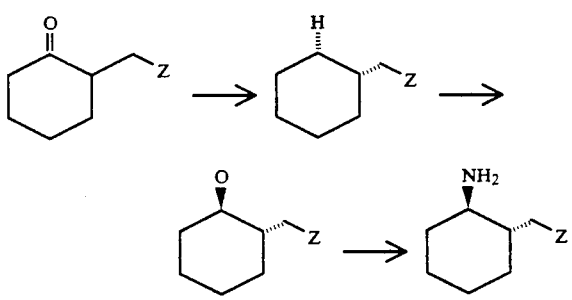

Where Q=N$_3$, phthalimide.

The following examples illustrate the preparation of the compounds of formula I.

EXAMPLE 1

N-[cis-2-(4-methylpiperidinomethyl)cyclohexyl]-4-amino-5-chloro-2-methoxybenzamide.

Carbonyldiimidazole (2.95 g; 18.2 mmoles) is added to a solution of 4-amino-5-chloro-2-methoxybenzoic acid (3.67 g; 18.2 mmoles) in THF (50 ml).

After stirring for one hour at ambient temperature, cis 2-(4-methylpiperidinomethyl) cyclohexylamine (3.83 g; 18.2 mmoles) is added as a solution in THF (15 ml). The reaction mixture is stirred overnight at ambient temperature. The mixture is evaporated under reduced pressure. The residue is taken up in methylene chloride and washed with an 8% aqueous solution of sodium bicarbonate and then with water.

The organic phase is dried over sodium sulphate and the solvent is driven off under reduced pressure to give crystals (5.87 g; 83%), which are recrystallised from isopropyl ether/acetone (8/2) mixture.

Melting point: 141°-142° C.
IR: (C=O): 1638 cm$^{-1}$ (CHCl$_3$)

EXAMPLE 2

N-[cis-2-(4-methylpiperidinomethyl)cyclohexyl]-4-amino-5-chloro-2-methoxybenzamide hydrochloride hydrate.

The product obtained from the preceding example (4.56 g) is dissolved in absolute ethanol (15 ml) and treated with a 4 N solution of hydrochloric acid in ethyl ether (4.3 ml). The mixture is concentrated and the hydrochloride is crystallised in the form of the hydrate (5.4% of water) by the addition of water (30 ml).

Melting point: 58°–145° C. (decomposition).
IR: (C=O): 1627 cm$^{-1}$ (KBr).

EXAMPLE 3

N-[trans-2-(4-methylpiperidinomethyl)cyclohexyl]-4-amino-5-chloro-2-methoxybenzamide dihydrochloride.

The product is prepared as in Example 1 using trans-2-(4-methylpiperidinomethyl)cyclohexylanine. The product is purified by chromatography on a silica column eluting with a methylene chloride/ethyl acetate/methanol/ammonia system (85/15/5/0.3). The oil obtained is treated with chloroethane, the solvent is evaporated and the residue is taken up in acetone to give crystals.

m.p.: 182°–184° C.
IR: (C=O): 1646 cm$^{-1}$ (KBr).

EXAMPLE 4

N-[cis-2-(4,4-dimethylpiperi-dinomethyl)cyclohexyl]-4-amino-5-chloro-2-methoxybenzamide hydrochloride hemihydrate.

The product is prepared as in Example 3 from cis-2-(4,4-dimethylpiperidinomethyl)cyclohexylamine.

m.p.: 132°–153° C. (dec.)
IR: (C=O): 1617 cm$^{-1}$ (CHCl$_3$)

The other compounds are obtained by identical methods using benzoic acid and the corresponding cyclohexylamine derivative. For 3-chloro-2,4,6-trimethoxybenzoic acid, the acid chloride is used as intermediate active species. The characteristics of these compounds are listed in Table I.

TABLE 1

| Ex. No. | R$_1$,R$_2$,R$_3$,R$_4$ | Z (configuration) | Salt | Melting Point °C. | Purification | IR cm$^{-1}$ |
|---|---|---|---|---|---|---|
| 5 | 4-amino-5-chloro-2-methoxy | piperidino (cis) | base | 153–170 (dec) | Chromatography SiO$_2$ | 1637, 1617 (CHCl$_3$) |
| 6 | " | piperidino (trans) | base | 100–113 | Chromatography SiO$_2$ | 1604, 1616 (CHCl$_3$) |
| 7 | " | 4-ethylpiperidino (cis) | HCl | 162–173 (dec) | Acetone/acetonitrile | 1616 (CHCl$_3$) |
| 8 | " | 4-propylpiperidino (cis) | HCl | 192 (dec) | EtOH/H$_2$O | 1616 (CHCl$_3$) |
| 9 | " | 4-t-butylpiperidino (cis) | HCl H$_2$O | 140–167 (dec) | H$_2$O | 1623 (KBr) |
| 10 | " | 3,5-dimethylpiperidino (cis) | HCl H$_2$O | 142–152 (dec) | H$_2$O | 1628 (KBr) |
| 11 | " | 4-methyl-4-ethylpiperidino (cis) | HCl 1.5 H$_2$O | 185–190 | H$_2$O | 1623 (KBr) |
| 12 | " | 4-methoxyethylpiperidino (cis) | base | 98–106 | petroleum ether/ethyl acetate | 1637–1617 (CHCl$_3$) |
| 13 | 3-chloro-2,4,6-trimethoxy | piperidino (cis) | HCl | 220–230 | acetone | 1623 (KBr) |
| 14 | " | piperidino (trans) | base | 212–214 (dec) | chromatography SiO$_2$ | 1648 (CHCl$_3$) |
| 15 | " | 4-methylpiperidino (cis) | HCl | 228–236 | chromatography Al$_2$O$_3$ | 1685–1596 (wide) (KBr) |
| 16 | " | 4-methylpiperidino (trans) | base | 120–121 | chromatography SiO$_2$ | 1648 (CHCl$_3$) |

| No. | R$_1$,R$_2$,R$_3$,R$_4$ | Z (configuration) | Salt | Melting Point °C. | Purification | IR (cm$^{-1}$) | $[\alpha]_D^{20°}$ = (C %) |
|---|---|---|---|---|---|---|---|
| 17 | 4-amino-5-chloro-2 ethoxy | 4-methyl piperidino (cis) | base | 137,5–138,5 | Acetone/ethyl ether | 1636–1616 (CHCl$_3$) | / |
| 18 | 4-amino-5-chloro-2-cyclopropyl methoxy | 4-methyl piperidino (cis) | HCl | 220–278 dec | H$_2$O | 1616 (KBr) | / |
| 19 | 4-amino-5-chloro-2 propyloxy | 4-methyl piperidino (cis) | HCl | 213–241 dec | H$_2$O | 1615 (KBr) | / |
| 20 | 4-amino-5-chloro-2 ipropyloxy | 4-methyl piperidino (cis) | HCl | 126–135 dec | H$_2$O | 1627 (KBr) | / |
| 21 | 4-amino-5-chloro-2-allyloxy | 4-methyl piperidino (cis) | HCl | 144–147 | H$_2$O | 1618 (KBr) | / |
| 22 | 4-amino-5-chloro-2-methoxy ethoxy | 4-methyl piperidino (cis) | HCl | 191–258 dec | H$_2$O | 1614 (KBr) | / |
| 23 | 4-amino-5-chloro-2-methoxy | 4-methyl piperidino (R,R) | HCl | 188–224 dec | H$_2$O | 1624 (KBr) | −97,8 (1, MeOH) |
| 24 | 4-amino-5-chloro-2-methoxy | 4-methyl piperidino (S,S) | HCl | 187–223 dec | H$_2$O | 1627 (KBr) | +98,3 (1, MeOH) |
| 25 | 4-amino-5-chloro-2-cyclopropyl methoxy | 4-methyl piperidino (R,R) | base | 151–153 | CH$_2$Cl$_2$/Et$_2$O | 1636–1617 (CHCl$_3$) | −65,8 (1, MeOH) |
| 26 | 4-amino-5-chloro-2-cyclopentyloxy | 4-methyl piperidino (cis) | HCl | 239–258 dec | H$_2$O | 1624 (KBr) | |
| 27 | 4-amino-5-chloro-2-isobutyloxy | 4-methyl piperidino (cis) | HCl | 136–143 dec | H$_2$O | 1627 (KBr) | / |

| No. | R$_1$,R$_2$,R$_3$,R$_4$ | Z (configuration) | Salt | Melting Point °C. | Purification | IR (cm$^{-1}$) |
|---|---|---|---|---|---|---|
| 28 | 4-amino-5-chloro-2-methoxy | 4-hydroxypiperidino (cis) | HCl | 254–263 dec | acetone/water | 1629 (KBr) |
| 29 | " | 4-ethoxypiperidino (cis) | HCl | 160–166 | H$_2$O | 1618 (KBr) |
| 30 | " | 4-methoxymethyl- | base | 148–149 | acetone/petroleum | 1638–1617 |

TABLE 1-continued

| 31 | " | piperidino (cis) 4-hydroxyethyl- piperidino (cis) | HCl | 138–143 | ether acetone | (CHCl₃) 1629 (KBr) |

Ar—CONH—[cyclohexyl]—Z

| No. | Ar | Z (configuration) | Salt | Melting Point °C. | Purification | IR (cm⁻¹) |
| --- | --- | --- | --- | --- | --- | --- |
| 32 | 7-(2,3-dihydro)benzofuranyl | 4-methylpiperidino (cis) | HCl | 177–181 | acetone | 1643 (KBr) |
| 33 | 7-(2,3-dihydro)benzofurnayl | 4-hydroxypiperidino (cis) | HCl | 233–238 dec | H₂O | 1651 (CHCl₃) |

The following examples illustrate the preparation of the cyclohexylamines of formula VII.

EXAMPLE A

Cis-2-(4-methylpiperidinomethyl)cyclohexylamine.

a) 1-[cis(2-trifluoroacetamidocyclohexylcarbonyl)]-4-methylpiperidine.

Cis-2-trifluoroacetamidocyclohexanecarboxylic acid chloride (8.61 g; 33 mmoles) in solution in benzene (50 ml) is treated dropwise with 4-methylpiperidine (8.3 g; 83 mmoles) dissolved in benzene (20 ml). The reaction mixture is kept at ambient temperature for 1 h 30 before evaporating the solvent. The residue is taken up in chloroform and the organic phase is washed with water, dried over sodium sulphate and then evaporated under reduced pressure. The product obtained is recrystallised from a benzene/petroleum ether mixture. m.p.: 135.5° C.

IR: (C=O): 1718–1621.5 cm⁻¹ (CHCl₃)

b) 1-[Cis(2-aminocyclohexylcarbonyl]-4-methylpiperidine.

1-[Cis(2-trifluoroacetamidocyclohexyl)carbonyl]-4-methylpiperidine (8.8 g: 0.027 mol) is dissolved in 95% ethanol (250 ml) and a 1 N solution of sodium hydroxide in 95% ethanol (50 ml; 0.05 mol) is then added.

The reaction mixture is stirred for 48 h at ambient temperature and then evaporated under reduced pressure. The residue is taken up in chloroform, washed with 1N NaOH and the organic phase is dried over Na₂SO₄ and evaporated to give a yellowish oil.

IR (C=O): 1621 cm⁻¹ (CHCl₃)

c) Cis-2-(4-methylpiperidinomethyl)cyclohexylamine.

1-[Cis-(2-aminocyclohexyl)carbonyl]-4-methylpiperidine (6.57 g; 0.0293 mol) is dissolved in tetrahydrofuran (25 ml) and added dropwise to a suspension of AlLiH₄ (2.22 g; 0.0586 mol) in tetrahydrofuran (50 ml). At the end of the addition, the reaction mixture is refluxed for 24 h and then hydrolyzed by carefully adding water (2.3 ml), then a 15% sodium hydroxide solution (2.3 ml) and then water (5 ml).

The aluminium salts are removed by filtering off and the tetrahydrofuran is evaporated under vacuum. The residue is taken up in an acid solution rendered alkaline using a 15% sodium hydroxide solution and extracted with chloroform. The organic phase is dried over Na₂SO₄ and evaporated under vacuum. The residue is purified by distillation.

b.p (27 Pa): 86°–87° C.

EXAMPLE B

Cis-2-(4,4-dimethyl-piperidinomethyl)cyclohexylamine.

a) 1-[Cis-2-trifluoro-acetamidocyclohexyl)-carbonyl]-4,4-dimethylpiperidine.

The product is obtained using the method described in Example A a) using 4,4-dimethylpiperidine. The residual oil is crystallised from a petroleum ether/ethyl acetate (80/20) mixture. m.p.: 97°–106° C. IR (C=O): 1717.8–1622.0 cm₋₁ (CHCl₃)

b) 1-[Cis (2-aminocyclohexyl)carbonyl]-4,4-dimethylpiperidine.

The product obtained in a) is detrifluoroacetylated using the method described in Example A b) to give an oil.

IR (C=O): 1621 cm⁻¹ (ChCl₃).

c) Cis-2-(4,4-dimethyl-piperidinomethyl)cyclohexylamine.

1-[Cis-(2-aminocyclohexyl)carbonyl]-4,4-dimethyl-piperidine is reduced by AlLiH₄ using the procedure described in Example A c). The oil obtained is distilled.

b.p. (53 Pa): 112° C.

The other cis cyclohexylamine derivatives are obtained by the same procedures and are reported in Table II.

TABLE II

| Example No. | Z | a) m.p.* (°C.) | IRυ (C=O)cm⁻¹ | b) IRυ (C=O) cm⁻¹ | c) b.p.** °C. (Pa) |
| --- | --- | --- | --- | --- | --- |
| C | 1-piperidinyl | 134–137 | 1717; 1620 (CHCl₃) | | |
| D | 1-(4-ethyl) piperidinyl | 92–96 | 1719; 1621.5 (CHCl₃) | 1621.6 (CHCl₃) | 125 (27) |
| E | 1-(4-propyl)piperidinyl | 113–114 | 1718; 1621.7 (CHCl₃) | 1621.7 (CHCl₃) | 125 (27) |

TABLE II-continued

| | | | | | |
|---|---|---|---|---|---|
| F | 1-(4-t-butyl)piperidinyl | 151–152 | 1719; 1621.7 (CHCl$_3$) | 1622 (CHCl$_3$) | 150 (66) |
| G | 1-(4-ethyl-4-methyl)piperidinyl | 91–94 | 1718.3; 1621.7 (CHCl$_3$) | 1621.7 (CHCl$_3$) | 150 (53) |
| H | 1-(3,5-dimethyl)piperidinyl | 118 | 1716; 1629 (KBr) | 1623 (CHCl$_3$) | |
| I | 1-(4-methoxyethyl)piperidinyl | 94.5 | 1718; 1622 (CHCl$_3$) | 1622 (CHCl$_3$) | 125 (53) |

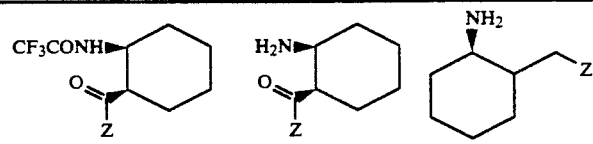

| Example No. | Z | Melting point °C. | IR δ cm$^{-1}$ | IR δ cm$^{-1}$ | b.p. |
|---|---|---|---|---|---|
| J | 1-(4-hydroxy)piperidinyl | 135 | 1718–1625 (CHCl$_3$) | 1624 (CHCl$_3$) | ND oil |
| K | 1-(4-hydroxyethyl)piperidinyl | oil | 1717–1623 (CHCl$_3$) | 1622 (CHCl$_3$) | ND oil |
| L | 1-(4-ethoxy)piperidinyl | 94–96 | 1719–1624 (CHCl$_3$) | 1625 (CHCl$_3$) | 137.5° C. (0.4 mmHg) |
| M | 1-(4-methoxymethyl)-piperidinyl | 132–133 (CHCl$_3$) | 1718–1624 (CHCl$_3$) | 1624 | ND oil |

*Kofler stage
**Büchi bulb oven
ND: Not distilled

EXAMPLE N

Trans-2-(4-methylpiperidinomethyl)cyclohexylamine.

a) 2-(4-methylpiperidinomethyl)cyclohexylamine.

Cyclohexanone (47.5 g; 0.484 mol) is dissolved in 95% ethanol containing formaldehyde (36 g of a 37% aqueous solution), hydrochloric acid (1.7 ml of a 37% aqueous solution), hydrochloric acid (1.7 ml of a 36% aqueous solution) and 4-methylpiperidine (40 g; 0.4 mol). the solution is refluxed for four hours. The ethanol is evaporated under vacuum and the residue is taken up in a 2N hydrochloric acid solution. The aqueous phase is washed with ether, rendered alkaline using a 15% aqueous sodium hydroxide solution and then extracted with methylene chloride. The organic phase is dried over Na$_2$SO$_4$ and the solvent is then driven off under vacuum. The oil obtained is distilled. b.p. (27 Pa): 85°–90° C.

IR (C=O): 1706 (CHCl$_3$)

b) 2-(4-methylpiperidinomethyl)cyclohexanone oxime.

2-(4-methylpiperidinomethyl)cyclohexanone (20.8 g; 0.1 mol) is dissolved in ethanol (100 ml). Hydroxylamine hydrochloride (7.54 g: 0.109 mol) dissolved in water (15 ml) is added to this solution. The reaction mixture is stirred for 1 h at ambient temperature. The solvent is evaporated under vacuum and the residue is taken up in chloroform and washed with a 2 N aqueous sodium hydroxide solution. The organic phase is dried over Na$_2$SO$_4$ and evaporated to give a white powder.

m.p.: 113°–116.5° C.

c) 2-(4-methylpiperidinomethyl)cyclohexylamine.

The oxime (13.5 g; 0.06 mol) obtained in the preceding example is dissolved in amyl alcohol (200 ml). Sodium (8.33 g; 0.36 mol) is added in small amounts so as to maintain gentle boiling. At the end of the addition, the reaction mixture is cooled and then acidified using a 2N aqueous HCl solution. The aqueous phase is extracted with ethyl acetate, rendered alkaline using a 15% sodium hydroxide solution and then extracted with methylene chloride. The organic phase is dried over Na$_2$SO$_4$ and then evaporated. The residual oil is distilled. b.p. (27 Pa): 94°–98° C. The product obtained contains about 75% of trans-2-(4-methylpiperidinomethyl)-cyclohexylamine. The pure diastereoisomer is isolated at the benzamide stage.

EXAMPLE O (S,S)- and (R,R)-2-(4-methylpiperidinomethyl)cyclohexylamine.

a) 1-[2(R)-benzamide-(S)-cyclohexylcarbonyl]-4-methylpiperidine.

2-(R)-benzamide-(S)-cyclohexylcarboxylic acid (8.87 g) is dissolved in 200 ml of tetrahydrofuran. After adding carbonyldiimidazole (5.82 g), the reaction mixture is stirred for 1 h 30 at ambient temperature. A solution of 4-methylpiperidine in 20 ml of tetrahydrofuran is added and the reaction mixture is stirred for a further 48 hours. The solvent is driven off under vacuum and the residue is taken up in methylene chloride. The organic phase is washed with twice 50 ml of 1N HCl, twice 50 ml of 1N NaOH and then twice 50 ml of water, dried over Na$_2$SO$_4$ and evaporated under reduced pressure. 11.16 g (94%) of oil are obtained. $[\alpha]_{578}^{20} = -47.9°$ (C=1, MeOH);

IR: =1731 weak, 1648, 1620 cm$^{-1}$ (CHCl$_3$)

a) 1-[2(S)-benzamido-(R)-cyclohexylcarbonyl]-4-methylpiperidine is obtained from the antipode as here by the same procedure. $[\alpha]_{578}^{20} = +49.2°$; (c=1, MeOH);

IR=1730 (weak), 1648, 1619 cm$^{-1}$ (CHCl)$_3$.

b) N-benzoyl-2(R)-(4-methylpiperidinomethyl)-(R)-cyclohexylamine.

The product obtained in step a) (10.38 g) dissolved in 20 ml of tetrahydrofuran is added dropwise to a suspension of AlLiH$_4$ (2.4 g) in 130 ml of tetrahydrofuran cooled to 0° C. At the end of the addition, the mixture is heated at 60° C. for 45 minutes. The mixture is cooled and then hydrolysed using a 1N aqueous NaOH solution (12 ml). The insoluble matter is removed by filtering off and the filtrate is evaporated under vacuum. The residue is dissolved in 1N hydrochloric acid. The aqueous phase is washed with ethyl acetate and then rendered alkaline using 2N sodium hydroxide solution The product is extracted with ethyl acetate. The organic phase is dried over Na$_2$ SO$_4$ and then evaporated under reduced pressure. The desired product is crystallised from a petroleum ether/ethyl acetate (95/5) mixture and collected by filtering off=6.53 g (65%). $[\alpha]_{578}^{20} = -67.1°$ (c=1, MeOH). m.p.=89°–91° C.

b') N-benzoyl-2(S)-(4-methylpiperidinomethyl)-(S)-cyclohexylamine is obtained by the same procedure from the product obtained in a'). $[\alpha]_{578}^{20} = +67.2°$ m.p.=79.5°–84.5° C.

c) (R,R)-2-(4-methylpiperidinomethyl)-cyclohexylamine.

The product obtained in step b) (6.43 g) is dissolved in 55 ml of 6N HCl. The mixture is refluxed for 5 days. The mixture is extracted with ethyl acetate, rendered alkaline using a concentrated sodium hydroxide solution and extracted with three times 100 ml of ethyl acetate. The organic phase is dried over $Na_2SO_4$ and then evaporated under reduced pressure. The diamine is obtained in the form of an oil (4.17 g; 97%). $[\alpha]_D^{20} = -25.2°$ (c=1, MeOH).

c') The same procedure yields (S,S) 2-(4-methylpiperidinomethyl) cyclohexylamine from the product obtained in b'). $[\alpha]_D^{20} = +25.2°$ (c=1, MeOH).

Results demonstrating the properties of the compounds of formula I in two tests, that is to say gastric emptying of solids and antagonism to stereotypy induced by apomorphine, are given below. The first test enables the activity of the product on the digestive motility to be demonstrated and the second permits confirmation of the absence of central dopaminergic antagonistic effects.

Activity on the digestive motility

Gastric emptying is studied in male Sprague Dawley rats weighing about 150 g. On day 0 a postdiaphragmatic vagotomy is carried out so as to create a retarded gastric emptying model. On day 7 the product to be tested or the placebo is administered to the animals oesophageally or intraperitoneally (T0). At T+15 minutes, n indigestible particles 1 mm in diameter are administered intragastrically. The animals are killed by euthanasia at T+3 h and the particles remaining in the stomach are counted. Gastric emptying is expressed by the percentage of particles having left the stomach.

It is less than 30% in the case of the rats which have undergone a vagotomy; in comparison, it is greater than 50% in the animals which have undergone a laparotomy only.

At least 3 doses are tested for each compound (the minimum of 10 animals per dose) and a positive control (metoclopramide, 5 mg $kg^-$) is always carried out in parallel. The statistic comparisons make use of the Mann and Whitney non-parametric test.

The results obtained are given in Table III. When a product proves active, its minimum effective dose (MED) and the potentialisation (in the form of a multiple of the control value) observed at this dose are determined. If the product is active from the lowest dose tested, the MED is said to be less than or equal to ($\leqq$) this dose.

Central dopaminerqic antagonist activity

Stereotypy of the buccal sphere is induced in male Sprague Dawley rats weighing about 150 g by subcutaneous injection of apomorphine hydrochloride (1 mg $kg^{-1}$). The products to be studied are administered intraperitoneally 30 minutes before the injection of apomorphine. The animals are observed 15, 30, 45, 60, 75 and 90 minutes after this injection.

The stereotypy intensity is assessed using a grading system ranging from 0 (absence of abnormal movement) to 3 (licking and/or intense or permanent chewing) and expressed in the form of a cumulative score over a period of 90 minutes.

At least 2 doses are tested for each product (a minimum of 6 animals per dose) and a positive control (metoclopramide, 3 mg $kg^{-1}$) is always carried out in parallel. The statistical comparisons make use of the Mann and Whitney non-parametric test. The results obtained are given in Table III. If the products are inactive (IN), the highest dose tested is indicated; if a product proves active, the effective dose (ED) and the percentage inhibition observed are indicated.

TABLE III

| Example | Gastric emptying of solids | | Antagonism to stereotypy induced by apomorphine |
|---|---|---|---|
| | MED ($\mu gkg^{-1}$) | Potentialisation | ED ($mgkg^{-1}$) |
| 2 | $\leqq 10$ | ×2.5 | IN(3) |
| 3 | 30 | ×2.5 | IN(3) |
| 4 | $\leqq 10$ | ×3.4 | IN(3) |
| 5 | $\leqq 30*$ | ×3.1 | IN(3) |
| 6 | 300* | ×1.9 | IN(3) |
| 7 | $\leqq 30$ | ×3.9 | IN(3) |
| 8 | $\leqq 30$ | ×2.3 | IN(3) |
| 9 | $\leqq 10$ | ×3.3 | IN(3) |
| 10 | $\leqq 10$ | ×6.1 | IN(3) |
| 11 | $\leqq 10$ | ×5.4 | IN(3) |
| 12 | 30 | ×2 | IN(3) |
| 13 | $\leqq 30$ | ×4.2 | IN(3) |
| 14 | 1000* | ×2.6 | IN(3) |
| 15 | 30 | ×5.7 | IN(3) |
| 16 | 3000* | ×3.2 | IN(3) |
| Compound A GB-A-1 015 921 | 3000 | ×1.18** | |
| 17 | 30 | 1.5 | IN(3) |
| 18 | 10 | 2.5 | IN(10) |
| 19 | 10 | 2.8 | ND |
| 20 | 10 | 3.1 | ND |
| 21 | 10 | 1.9 | ND |
| 22 | 30 | 1.6 | ND |
| 23 | <10 | 1.7 | IN(3) |
| 24 | 30 | 2 | IN(3) |
| 25 | 30 | 1.7 | IN(3) |
| 27 | 10 | 2.1 | ND |

TABLE III-continued

| Example | Gastric emptying of solids | | Antagonism to stereotypy induced by apomorphine |
|---|---|---|---|
| | MED ($\mu gkg^{-1}$) | Potentialisation | ED ($mgkg^{-1}$) |
| 28 | <10 | 2.1 | IN(10) |
| 29 | 30 | 2.7 | ND |
| 30 | 10 | 1.9 | IN(3) |
| 31 | 30 | 2.7 | IN(3) |
| 32 | 50 | ×7 | IN(1) |
| 33 | 30 | 2.6 | ND |

*products studied after intraperitoneal administration
**not significant
ND: Not determined The compounds of formula (I) may be used to stimulate the gastro-intestinal motility. They may be used to treat digestive disorders such as gastroparesis, gastro-oesophaeal reflux, dyspepsia, constipation and some forms of irritable colon or intestine syndrome.

These compounds or their addition salts obtained with pharmaceutically acceptable acids can be administered to man in the form of a wide variety of pharmaceutical compositions.

The present invention therefore also relates to therapeutic compositions comprising, as active principle, a compound of formula I or one of its addition salts with pharmaceutically acceptable acids.

The active principle may be administered orally, intravenously, subcutaneously or parenterally and in one of more administrations for a daily dose of 0.05 mg to 50 mg.

The therapeutic compositions may contain 0.05 to 50 mg of active principle per unit. For oral administration, they may be in the form of tablets or of capsules containing one of the excipients commonly used in the pharmaceutical sector.

We claim:

1. A compound selected from the compounds of the formula

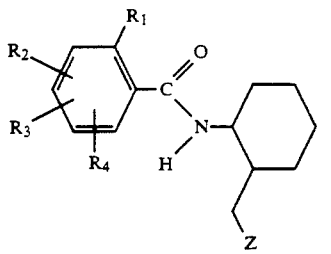

(I)

in which:

$R_1$ is selected from $C_1-C_4$ alkoxy, methoxy ($C_1-C_3$ alkoxy), $C_3-C_4$ alkenyloxy and $C_5-C_6$ cycloalkoxy, or $R_1$ and $R_2$, in the 3-position, together and with the aromatic ring to which they are bonded form a 2,3-dihydrobenzofuran ring, $R_2$, $R_3$ and $R_4$ are selected independently of one another from hydrogen, halogen, hydroxy, $C_1-C_3$ alkoxy, amino, ($C_1-C_3$ alkyl)amino, di($C_1-C_3$ alkyl) amino and ($C_1-C_3$ alkyl) carbonylamino, and Z is selected from piperidinyl and piperidinyl substituted in the 4-position by hydroxy, $C_1-C_3$ alkoxy, hydroxyethyl, ($C_1-C_3$ alkoxy)ethyl, ($C_1-C_3$ alkoxy)methyl, $C_1-C_4$ alkyl or two $C_1-C_3$ alkyl, and their addition salts with pharmaceutically acceptable acids.

2. A compound selected from the compounds of the formula:

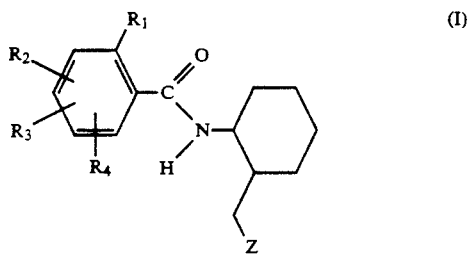

(I)

in which:

$R_1$ is selected from $C_1-C_4$ alkoxy, methoxy($C_1-C_3$ alkoxy), $C_3-C_4$ alkenyloxy and $C_5-C_6$ cycloalkoxy, or $R_1$ and $R_2$, in the 3-position, together and with the aromatic ring to which they are bonded form a 2,3-dihydrobenzofuran ring, $R_2$, $R_3$ and $R_4$ are selected independently of one another from hydrogen, halogen, hydroxy, $C_1-C_3$ alkoxy, amino, ($C_1-C_3$ alkyl)amino, di($C_1-C_3$ alkyl)amino and ($C_1-C_3$ alkyl)carbonylamino, and Z is selected from piperidinyl and piperidinyl substituted in the 4-position by hydroxy, $C_1-C_3$ alkoxy, ($C_1-C_3$ alkoxy)ethyl, ($C_1-C_3$ alkoxy)methyl groups, straight-chain or branched $C_1-C_4$ alkyl or two $C_1-C_3$ alkyl, and their addition salts with pharmaceutically acceptable acids.

3. A compound according to claim 1, of the formula:

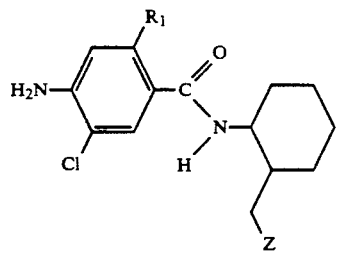

in which $R_1$ is $C_1-C_4$ alkoxy.

4. A compound according to claim 3, in which $R_1$ is methoxy.

5. A compound according to claim 3, in which $R_1$ is selected from ethoxy and cyclopropylmethoxy.

6. A compound according to claim 3, in which Z is selected from piperidino, 4-methylpiperidino, 4,4-dimethylpiperidino and 4-hydroxypiperidino.

7. A compound according to claim 6, of formula

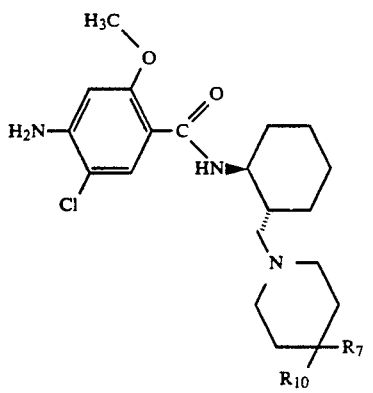

(IV)

or

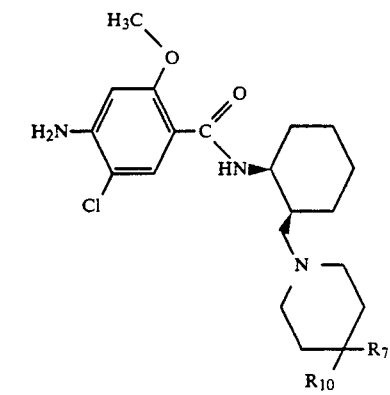

(V)

in which R₇ is methyl and R₁₀ is hydrogen.

8. A compound according to claim 6, of formula

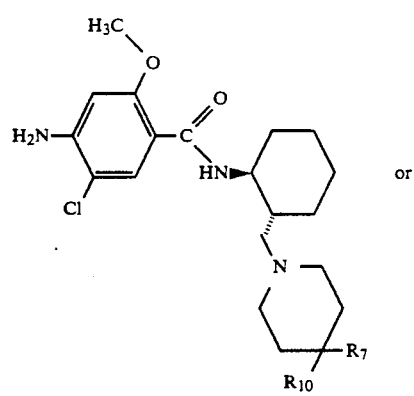

(IV)

or

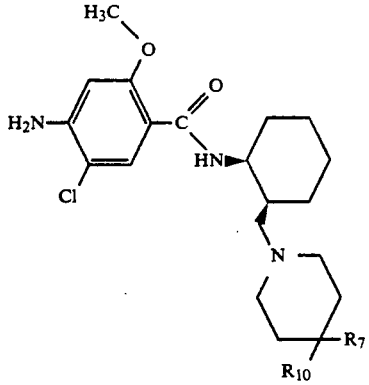

(V)

in which $R_7$ and $R_{10}$ are methyl.

9. A compound according to claim 6, of formula

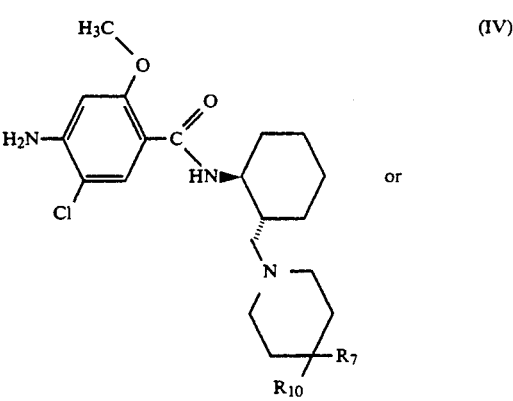

(IV)

or

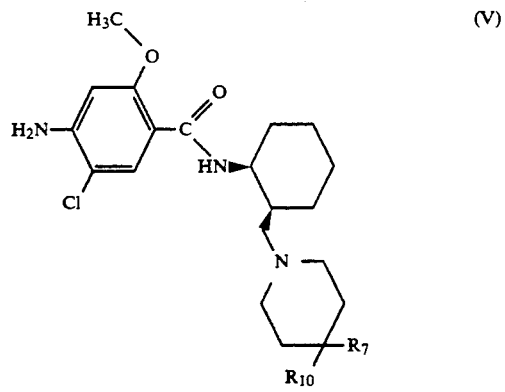

(V)

in which $R_7$ is hydroxy and $R_{10}$ hydrogen.

10. A therapeutic composition having a stimulating activity on the gastro-intestinal motility comprising an effective amount of a compound according to claim 1 and a pharmaceutically acceptable carrier.

11. A process for stimulating the gastro-intestinal motility which comprises administering to a human in need thereof an effective amount of a compound according to claim 1.

* * * * *